United States Patent [19]

Villez

[11] Patent Number: 4,917,695
[45] Date of Patent: Apr. 17, 1990

[54] DIAPER WITH LENGTHWISE ELASTICS AND METHOD FOR CONTINUOUS MANUFACTURE OF SUCH DIAPERS

[75] Inventor: Yves Villez, Linsells, France

[73] Assignee: Boussac Saint Freres B.S.F., La Madeleine, France

[21] Appl. No.: 127,465

[22] Filed: Dec. 2, 1987

[30] Foreign Application Priority Data

Dec. 2, 1986 [FR] France ................... 86 16844

[51] Int. Cl.⁴ .................. A61F 13/16; A41B 13/02
[52] U.S. Cl. ....................... 604/370; 604/385.1; 604/385.2; 604/386; 604/387; 604/393; 156/160; 156/163; 156/164; 156/229
[58] Field of Search ............ 156/161, 164, 176, 160, 156/163, 229; 604/358, 370, 385.1, 385.2, 386, 387, 393

[56] References Cited

U.S. PATENT DOCUMENTS

| | | | |
|---|---|---|---|
| 3,860,003 | 1/1975 | Buell | 604/385.2 |
| 4,081,301 | 3/1978 | Buell | 156/164 |
| 4,353,762 | 10/1982 | Bouda | 156/164 |
| 4,405,397 | 9/1983 | Teed | 156/164 |
| 4,525,229 | 6/1985 | Suzuki et al. | 156/161 |
| 4,578,071 | 3/1986 | Buell | 604/385.1 |
| 4,661,102 | 4/1987 | Shikata et al. | 604/385.2 |
| 4,666,542 | 5/1987 | De Jonckheere | 156/164 |

FOREIGN PATENT DOCUMENTS

| | | |
|---|---|---|
| 158490 | 10/1985 | European Pat. Off. . |
| 3319043 | 11/1984 | Fed. Rep. of Germany . |
| 2583620 | 12/1986 | France ................... 604/385.1 |

Primary Examiner—Michael W. Ball
Assistant Examiner—Jeff H. Aftergut
Attorney, Agent, or Firm—Owen, Wickersham & Erickson

[57] ABSTRACT

A diaper in which two strips of liquid-impervious supple sheet material are placed over the entire length of the diaper, over the elastic members secured by adhesive bonding in the stretched state onto the inner face of the liquid-impervious outer sheet on the said face provided with lengthwise lines of adhesive. The inner sheet, permeable to liquids, is coated with adhesive and is supplied, over the absorbent pad, onto the impervious sheet so as to adhere to the latter and to the strips all around the absorbent pad. The application particularly relates to diapers comprising an absorbent pad containing superabsorbent material in granular form.

4 Claims, 5 Drawing Sheets

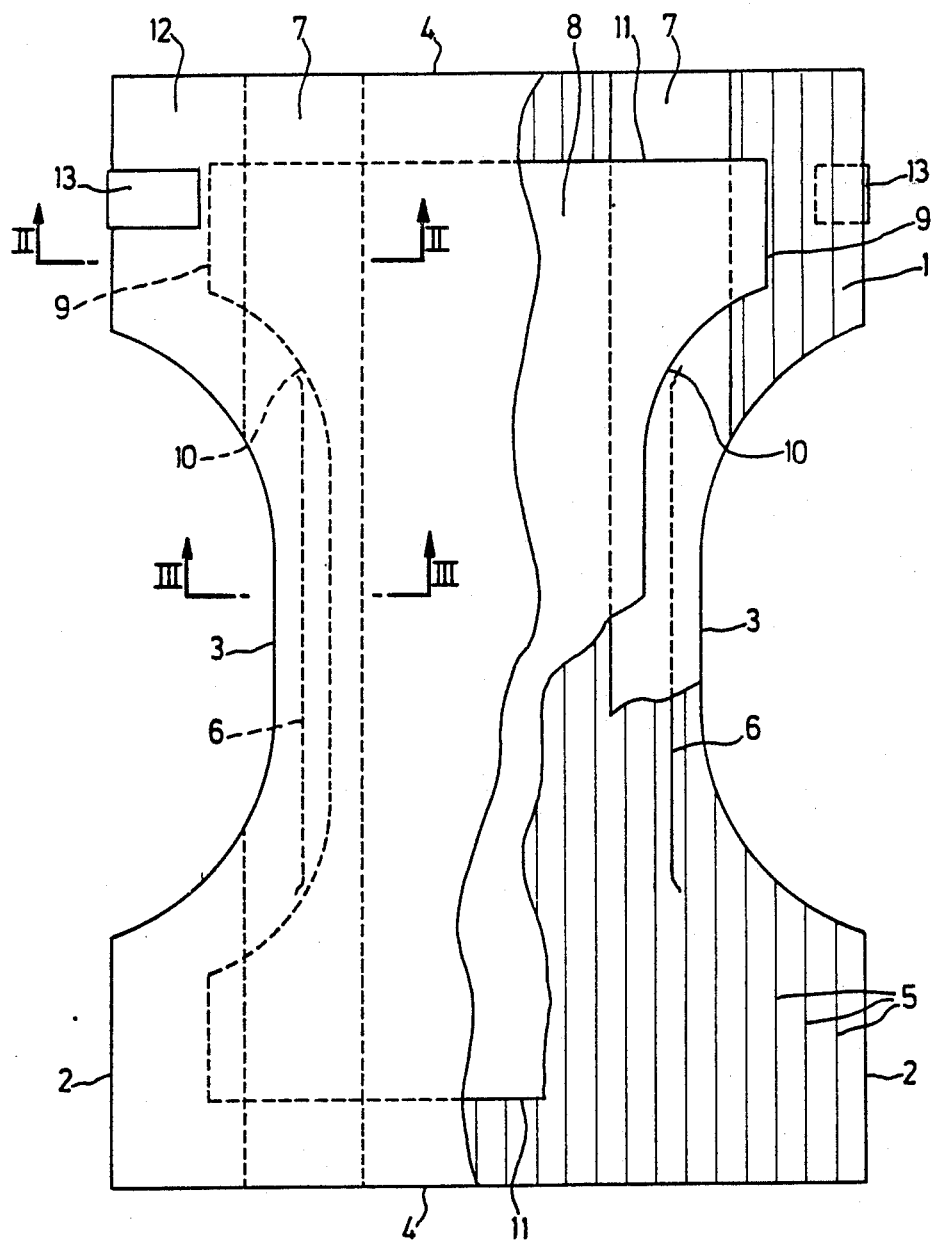

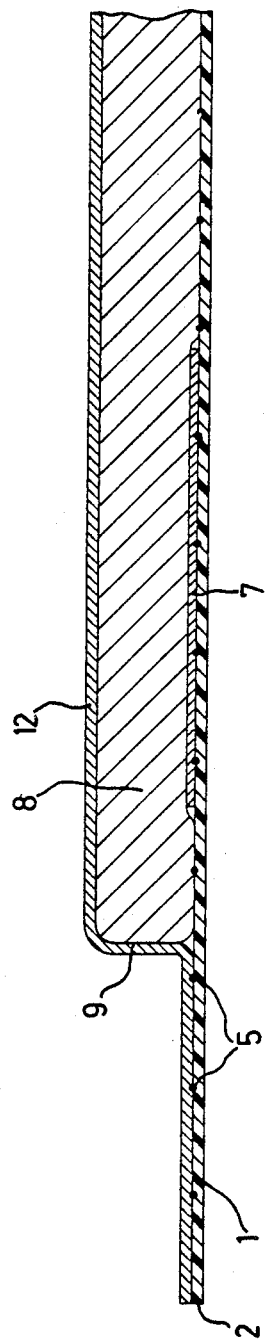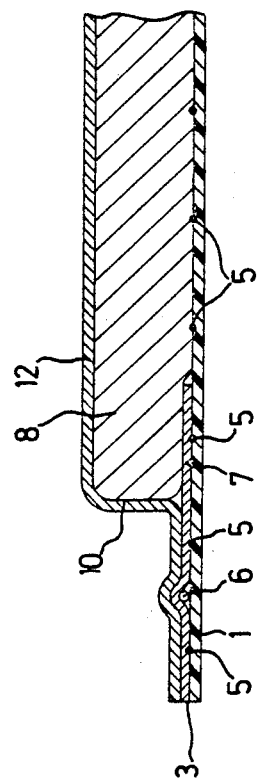

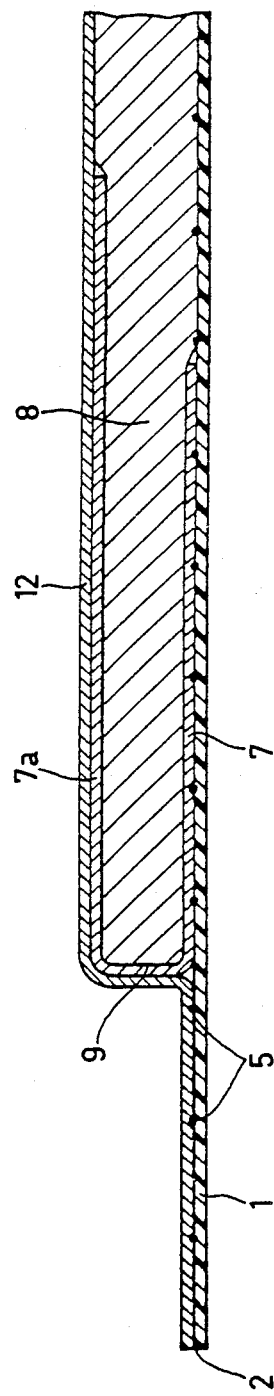
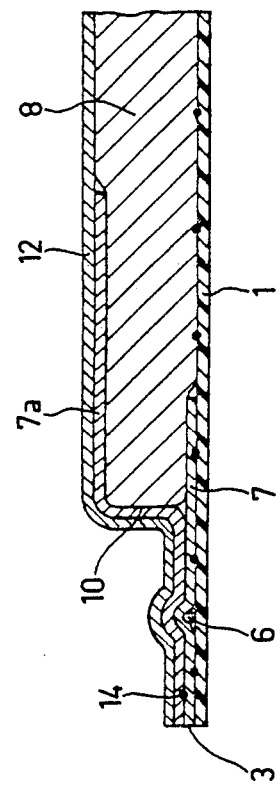

DIAPER WITH LENGTHWISE ELASTICS AND METHOD FOR CONTINUOUS MANUFACTURE OF SUCH DIAPERS

The present invention relates to nappy-pants of the type comprising a supple outer sheet, impervious to liquids, whose inner face is provided with lengthwise lines of adhesive, an absorbent pad arranged on the inner face of the outer sheet so that its two opposed lengthwise edges are set back relative to the two opposed lengthwise edges of the outer sheet and so that its two opposed transverse edges are set back relative to the two opposed transverse edges of the outer sheet, a supple inner sheet, permeable to liquids, covering the inner face of the outer sheet and the absorbent pad arranged on this face, lengthwise elastic members secured by adhesive bonding in the stretched state on the inner face of the outer sheet, along the median part of the two opposed lengthwise edges of this sheet, the inner sheet being secured by adhesive bonding to the outer sheet by virtue of an adhesive coating of its outer face in the region of contact of the sheets around the pad, and fastening means for closing the nappy-pants around the user's body.

The invention also relates to a process for continuous manufacture of such nappy-pants.

The known process for continuous manufacture of nappy-pants of the type defined above consists unwinding a continuous band of liquid-impervious sheet, applying continuous lengthwise lines of adhesive onto the upper face of the said band, unwinding continuous elastic members, coating the said elastic members with adhesive at intervals so as to provide adhesive-coated sections separated by sections not coated with adhesive, and in applying them in the stretched state onto the upper face of the band, impervious between the lines of adhesive in the vicinity of the two opposed lengthwise edges of the band, so as to make the elastic members adhere via successive sections at intervals to the band, impervious, successively depositing onto the upper face of the impervious band provided with the elastic members, individual absorbent pads of a width which is smaller than the width of the band so that the successive pads are arranged on the band in the regions where the elastic members adhere to the latter and are placed at a distance from each other in the direction of the length of the impervious band, unwinding a continuous band of sheet which is permeable to liquids having the same width as the impervious band, in coating the said band with adhesive on one face, and in applying it via the said adhesive-coated face onto the upper face of the impervious band already provided with elastic members and with absorbent pads, and successively cutting off in the transverse direction the two bands and the stretched elastic members, between the successive pads located at intervals, that is to say in the sections of the elastic members which are not coated with adhesive.

During this transverse cutting which provides the individual nappy-pants, the elastic members, initially continuous and kept in the stretched state, are sectioned, so that the parts of the elastic members arranged on each pair of nappy-pants on both sides of the adhesive-coated sections, adhering to the impervious sheet, contract, that is to say relax freely, while the adhesive-coated sections adhering to the outer sheet contract with the said sheet in order to give the latter, in the crotch region of the nappy-pants, the elasticity needed in order to ensure a good adaptation to the user's body, and good leakproofing.

However, in order to permit a free relaxation of the parts of the elastic members which are not coated with adhesive, when this sectioning takes place, it is also necessary to act so that these parts do not adhere to the adhesive-coated permeable sheet. This is the reason why, until now, in the adhesive coating of this permeable sheet, regions which are not coated with adhesive are provided at the location of the sections of the elastic members which are not coated with adhesive, before the sectioning.

This therefore gives rise, on the nappy-pants, in the region included between the transverse edges at a distance from the absorbent pad on the one hand, and from the permeable and impervious sheets on the other hand, to "tunnels" extending between these two sheets from the transverse edges of the pad as far as the transverse edges of the sheets, that is to say providing communication between the space included between the two sheets and the outside, and containing the absorbent pad. These "tunnels" not only promote the outward escape, by a draining action, of the urine absorbed by the pad, but also permit the outward escape of the particulate material forming the pad. This is the case, for example, with absorbent pads made of defibred cellulose pulp, but in particular with the pads containing superabsorbent material in granular form which, although being generally incorporated in another material, for example in defibred cellulose pulp, frequently separates very easily from the absorbent pad and can, by escaping through the "tunnels" in question, reach the outside and, because of its existence in the form of very fine and light particles in the dry state, give rise here to effects which are uncomfortable or even harmful to the users.

The subject of the present invention is nappy-pants of the type defined above in which the risk of outward escape of constituent material of the absorbent pad is prevented with certainty. Another subject of the invention is nappy-pants of the type defined above in which the outward escape, at the location of the transverse edges of the nappy-pants, of the liquids absorbed by the pad of the nappy-pants is prevented or at least greatly reduced. A further subject of the invention is nappy-pants in which the risk of escape of liquid on the lateral (lengthwise) edges of the absorbent pad is prevented or at least greatly reduced.

Lastly, another subject of the invention is a process for continuous manufacture of such nappy-pants.

The nappy-pants according to the invention comprise a supple outer sheet, impervious to liquids, whose inner face is provided with lengthwise lines of adhesive. The nappy-pants additionally comprise an absorbent pad arranged on the inner face of the outer sheet so that its opposed lengthwise edges are set back relative to the two opposed lengthwise edges of the outer sheet and its two opposed transverse edges are set back relative to the two opposed transverse edges of the outer sheet. The nappy-pants furthermore comprise a supple inner sheet, permeable to liquids, covering the inner face of the outer sheet and the absorbent pad arranged on this face. Fastening members are provided in order to close the nappy-pants around the user's body. Furthermore, lengthwise elastic members are secured by adhesive bonding in the stretched state onto the inner face of the outer sheet along the median part of the two lengthwise edges of the latter, the outer face of the inner sheet being secured by adhesive bonding to the inner face of the outer sheet, on the periphery of the absorbent pad, by virtue of an adhesive coating of the outer face of the inner sheet in the region of contact of the two sheets around the pad. Lastly, the nappy-pants comprise two strips of supple sheet which are placed on the inner face of the outer sheet, below the absorbent pad, over the elastic members, over the entire length of the outer sheet and over a width which is greater than the width of these elastic members, so that the strips are secured to the outer sheet by at least one lengthwise line of adhesive of the outer sheet, on both sides of the elastic members, the outer face of the inner sheet being coated with adhesive so as to adhere all around the pad onto the outer sheet and onto the strips in places where the said strips overlap the absorbent pad.

The two strips extending over the whole length of the outer sheet prevent any contact between the inner sheet, even though it is coated with adhesive on the whole periphery, and the elastic members contained in the "tunnels" which these strips form with the outer sheet, so that the parts of the elastic members which are not coated with adhesive can contract freely during the sectioning. Furthermore, the constituent material of the absorbent pad arranged above these strips cannot enter the said tunnels and escape outwards, since the tunnels are open only at the two transverse edges of the nappy-pants.

The strips forming the "tunnels" may consist of a material which is permeable to liquids, but in order to ensure that any escape through the said tunnels of the liquids absorbed by the pad is prevented, it is preferable for the strips to consist of a liquid-impervious material, so that the "tunnels" consist entirely of liquid-impervious materials.

The process for continuous manufacture of nappy-pants such as are defined above consists in unwinding a continuous band of liquid-impervious sheet, continuously applying lengthwise lines of adhesive at intervals transversely onto the upper face of the said impervious band, unwinding continuous elastic members, coating the said elastic members with adhesive at intervals to form adhesive-coated sections separated by sections which are not coated with adhesive, and in applying the elastic members in the stretched state onto the upper face of the impervious band, between the lengthwise lines of adhesive, in the vicinity of the two opposed lengthwise edges, so as to make the elastic members adhere thereto via successive sections at intervals, continuously unwinding and applying onto the upper face of the impervious band, over the elastic members, two continuous strips of sheets, each having a width greater than the width of the elastic members, so that each strip adheres to the impervious band via at least one lengthwise line of adhesive on both sides of the elastic members, successively depositing onto the upper face of the impervious sheet, over the strips, individual absorbent pads of a width smaller than the width of the band, so that the successive pads are arranged on the impervious band in the regions where the elastic members adhere to the band and are situated at a distance from each other in the direction of the length of the impervious band, unwinding a continuous liquid-permeable band, having substantially the same width as the impervious band, in coating the said permeable band with adhesive on one face and in applying it via the said adhesive-coated face onto the upper face of the impervious band, over the strips and the absorbent pads, and successively cutting off, in the transverse direction, the two bands, the stretched elastic members and the two strips, between the successive pads located at intervals, in the place of the sections of the elastic members which are not coated with adhesive.

Although it is possible to coat the band which is permeable to liquids with adhesive over its entire first face, it is also possible to coat this sheet with adhesive on its first face according to a repetitive pattern leaving, in the middle of the width of the band, successive windows which are not coated with adhesive, which are surrounded by complete adhesive-coated frames and which, when the permeable sheet is applied onto the impervious sheet, come into place on the absorbent pads arranged on the permeable sheet, while the adhesive-coated frames adhere to the impervious sheet and to the strips secured to the latter, over the entire periphery of the absorbent pad.

A more detailed description will be given below, with reference to the appended diagrammatic drawings, of two embodiments illustrating, without any limitation, a pair of nappy-pants according to the invention and a process for continuous manufacture of such nappy-pants; in the drawings:

FIG. 1 is a view on the inner face of nappy-pants according to the invention, which are shown flattened, the elastic members being stretched, with two partial cutaways showing the inner structure of the nappy-pants;

FIG. 2 is a section, on larger scale, along II—II of FIG. 1;

FIG. 3 is a section, on larger scale, along III—III of FIG. 1;

FIGS. 5 to 7 show, in a manner similar to FIGS. 1 to 3, another embodiment of a pair of nappy-pants according to the invention.

Figure 4:
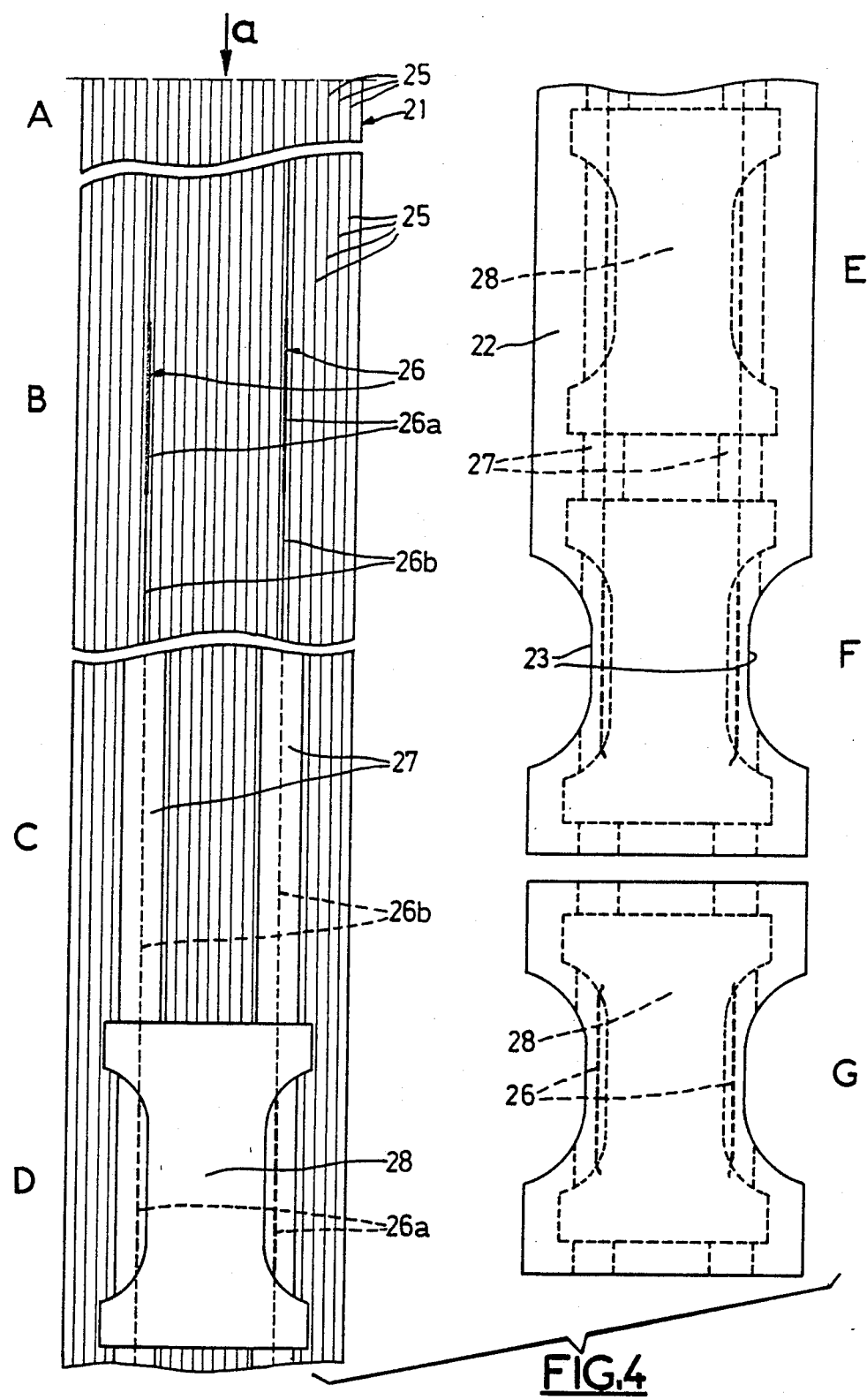
FIG. 4 shows the various stages of the continuous manufacture of nappy-pants according to FIGS. 1 to 3.

As illustrated by FIGS. 1, 2 and 3, the nappy-pants comprise a supple outer sheet 1, impervious to liquids, for example a sheet of plastic such as polyethylene assuming a generally rectangular shape with two opposed lengthwise edges 2 each provided with a median cutout 3, and two opposed transverse edges 4, which are rectilinear. On its inner face, which can be seen in FIG. 1, the sheet 1 is provided with a multitude of lengthwise lines of adhesive 5, at intervals.

A lengthwise elastic member 6 is secured in the stretched state, by adhesive bonding onto the inner face of the sheet 1, on the median part of the length of the sheet 1, along each cutout 3, with a slight set-back inwards relative to the bottom of the cutout.

A strip 7 of a supple sheet material, for example coated or uncoated paper or a sheet of plastic, is secured over the entire inner length of the sheet 1, along each of the two lengthwise edges of the latter, so as to cover each one of the elastic members 6. It should be noted that the width of the strip 7 is such that each strip 7 adheres to the sheet 1 along at least one line of adhesive 5 on both sides of the corresponding elastic member 6. Each strip 7 thus forms, with the sheet 1, a lengthwise tunnel containing the elastic member and extending over the entire length of the sheet 1, this tunnel being defined by the strip 7, the sheet 1 and two lines of adhesive 5 on both sides of the elastic member 6.

An absorbent pad 8, also generally rectangular in shape, with two opposed lengthwise edges 9 each provided with a median cutout 10, and two rectilinear opposed transverse edges 11, is secured onto the inner face of the sheet 1, over the strips 7, so that its lengthwise edges 9 and transverse edges 11 are set back relative to the lengthwise edges 2 and transverse edges 4 of the sheet 1. The absorbent pad 8 may consist, for example, of defibred cellulose pulp, containing or not containing superabsorbent material in granular form. The securing of the pad 8 onto the sheet 1 is produced by the lines of adhesive 5 which remain apparent after the placing of the strips 7.

On the inner face carrying the strips 7 and the absorbent pad 8, the whole of the sheet 1 is covered with a liquid-permeable voile 12, for example a nonwoven voile. On its side facing the sheet 1, this voile 12 is provided with an adhesive coating such that the sheet 12 adheres at least to the sheet 1 and to the strips 7 in the regions where the sheet 1 is covered by the strips 7, over the whole periphery of the absorbent pad 8, that is to say between the edges 9, 10, 11 of the pad 8 and the edges 2, 3, 4 of the sheet 1.

This adhesive coating applies either to the whole area of the sheet 12, in which case the latter also adheres to the absorbent pad 8, or else is applied according to a pattern in the shape of a closed frame surrounding a window, which may, for example, take a rectangular shape or the shape of the absorbent pad 8.

Lastly, adhesive fastenings 13 of known type are secured onto the two opposed lengthwise edges 2 of the nappy-pants formed in this manner, in the vicinity of one of the transverse edges 4, that is to say of a side of the two opposed cutouts 3, in order to permit the nappy-pants to be closed around the user's waist.

From FIGS. 1, 2 and 3 it can be seen that each strip 7 defines with the sheet 1, for each elastic member 6, over the entire length of the nappy-pants, a tunnel defined on both sides of the elastic member 6 by at least one line of adhesive 5. Consequently, these tunnels, extending over the whole length of the nappy-pants and opening outwards at the two transverse ends 4 of the nappy-pants, are completely isolated from the absorbent pad 8 arranged on the strips 7. In these conditions, the constituent material of the absorbent pad 8 cannot in any way enter the tunnel defined by the strips 7 and escape outwards therefrom.

In the case where the strips 7 consist of a liquid-impervious material, for example polyethylene or coated paper, these tunnels are not accessible to the liquids absorbed by the pad 8 either, thus preventing any escape of the liquids (illegible) through a draining action via the said tunnel, at two transverse ends of the nappy-pants, which ends correspond to the belt of the nappy-pants when the nappy-pants are closed.

A description will now be given, with reference to FIG. 4, of a preferred embodiment for the continuous manufacture of nappy-pants according to FIGS. 1 to 3.

In order to manufacture the nappy-pants continuously, a band 21 of liquid-impervious sheet is first continuously unwound, with a width corresponding to the width of the nappy-pants to be manufactured. A multitude of lengthwise lines of adhesive 25 placed at intervals over the entire width of the band 21 is applied onto the upper face of the band 21 unwound in this manner, moving forward in the direction of the arrow a (stage A).

Two continuous elastic members 26 are then continuously unwound, the said elastic members 26 are coated with adhesive at intervals so as to form adhesive-coated sections 26a separated by sections 26b which are not coated with adhesive, and the two elastic members are applied in the stretched state onto the upper face of the band 21, between the lines of adhesive 25, set back inwards relative to the two opposed lengthwise edges of the band, so as to make the elastic members 26 adhere, in the stretched state via the adhesive-coated sections 26a, to the band (stage B).

Two strips 27 of a material made of supple sheet which is permeable or impervious to liquids are then continuously unwound and are applied continuously onto the upper face of the band 21, over the two elastic members 26, the width of the strips 27 being such that each strip 27 is connected by at least one line of adhesive 25 to the band 21 on both sides of each elastic member 26 (stage C).

Absorbent pads 28, hourglass-shaped, with a width smaller than the width of the band 21, are then successively deposited onto the upper face of the band 21 provided with the elastics 26 and the strips 27, each pad 28 being arranged symmetrically relative to an adhesive-coated section 28a of the elastic members 26 and symmetrically relative to the two lengthwise edges of the band 21 (stage D).

A continuous band 22 of liquid-permeable supple sheet having the same width as the band 21 is then unwound, the band 22 is coated with adhesive on one face and is applied via the said adhesive-coated face onto the upper face of the band 21, over the pads 28, so that the band 22 adheres, all around the pads 28, to the band 21 and to the parts of the strips 27 which are not covered by the pads 28 (stage E).

Two opposed lateral cutouts 23 are then cut out from the two bands 21 and 22, in the middle of the length of each pad 28, from the two lengthwise sides of the bands 21 and 22 (stage F).

After adhesive fastenings, not shown in FIG. 4, have then been secured on the two lengthwise edges of the bands 21, 22 at the location of a wider part of each pad 28, the two combined bands 21 and 22, the stretched elastic members 26 and the strips 27 are then cut off transversely between the successive pads 28, that is to say in the sections which are not coated with adhesive 26b of the elastic members 26 (stages F and G).

The sectioning, at the location of the sections 26b which are not coated with adhesive, of the elastic members 26 which are hitherto maintained in the stretched state, has the result of releasing the elastic members 26 from their initial tension, so that the sections 26b which are not coated with adhesive relax while freely contracting, whereas the adhesive-coated sections 26a adhere both to the sheet 21 and to the strips 27 and thus can contract only together with the sheet 21 and the strips 27. FIG. 4 makes it possible to recognize (stage G) this free contraction of the parts of the elastic members which are not coated with adhesive, whereas the adhesive-coated parts of the elastic members are still stretched owing to the fact that the nappy-pants obtained by sectioning the composite band are still held in the extended state by means which are not shown. After release of the nappy-pants, the adhesive-coated parts of the elastic members relax, contracting the nappy-pants elastically in the length direction in the crotch region, of reduced width.

It is self-evident that the nappy-pants and the process for manufacture according to the invention, such as described above and illustrated by the drawing, have been given merely by way of illustrative example, without any limitation being employed, and that many modifications and alternative forms are possible within the scope of the invention.

Thus, the invention applies not only to hourglass-shaped nappy-pants but also to rectangular nappy-pants.

Instead of comprising a single elastic member on each lengthwise edge of the absorbent pad, the nappy-pants could also comprise groups of a number of parallel elastic members, for example two or four in number, each group of elastic members being covered by the same strip.

The outer sheet of the nappy-pants may consist of any supple sheet material, impervious to liquids and impervious or preferably permeable to air, for example a sheet of polyethylene, made permeable to air where appropriate.

The absorbent pad may be of any nature, but the invention is particularly advantageous in the case of nappy-pants comprising absorbent pads containing particulate matter, especially superabsorbent material in granular from which, in the known nappy-pants, is liable to escape, whereas this risk is completely eliminated in the nappy-pants according to the invention, by virtue of the presence of the strips 7, 27.

These strips may be made of any material permeable to liquids, for example paper, or preferably a liquid-impervious material, for example a sheet of coated paper, a sheet of plastic, and the like, preferably permeable to air.

Figure 5:
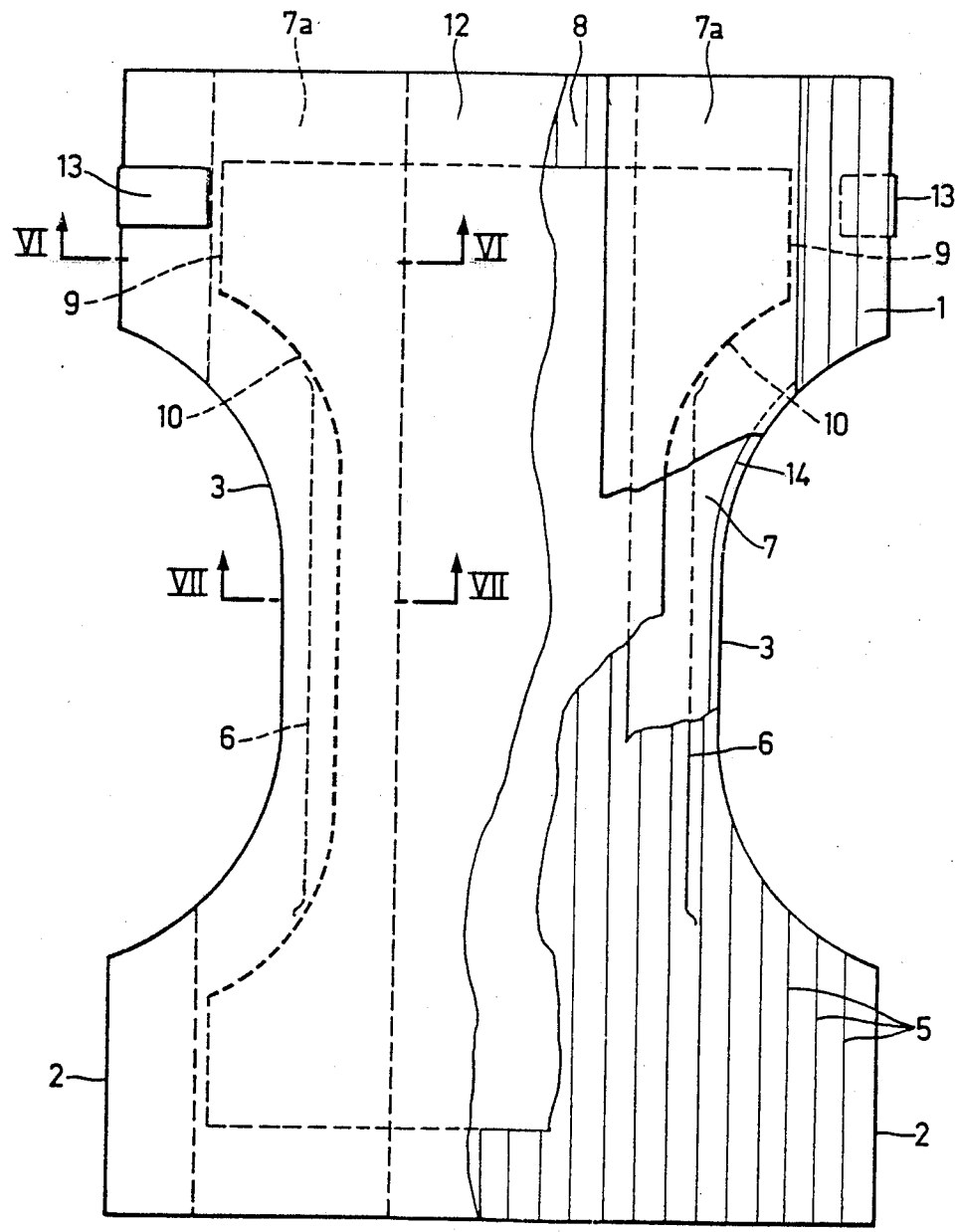

The nappy-pants according to the embodiment in FIGS. 5 to 7 differ from those of the embodiment in FIGS. 1 to 3 in that the strips 7 are wider so as to overlap the pad 8 laterally, and that the parts 7a of the strips overlapping the pad laterally are folded back onto the top of the pad 8. These parts 7a of the strips thus envelop the lateral edges of the pad over the entire length, that is to say at the place of the median cutouts 10 and on both sides of the median cutouts (regions 9). In the region of the sheet 1 and the voile 12, where the overlapping parts 7a of the strips 7 undergo cutting off at the location of the cutouts 3, the two superposed folds of the strips 7 are joined together by a weld line 14 produced by cutting out the cutouts by fusion, or by a line of adhesive applied before the folding back of the parts 7a. The strips 7, 7a thus envelope the lateral edges of the pad over the entire length, thus preventing any escape of liquid from the pad 8 at these edges. Moreover, the folded-back parts 7a of the strips 7 reduce the area of the pad 8 in contact with the user's skin via the voile 12.

Obviously, in this embodiment, the strips 7 are impervious to liquids.

The manufacture of the nappy-pants according to FIGS. 5 to 7 differs from that of the nappy-pants according to FIGS. 1 to 3, described with reference to FIG. 4, only in the use of wider bands 27, in an operation of folding back, onto the top of the pads 28, of the parts of the bands 28 overlapping the pads 28 laterally (between the stages C and D), and in the optional provision of lines of adhesive on the strips, before the folding back (lines 14).

The special advantage of nappy-pants of this kind, compared with nappy-pants according to French Patent Application No. 2,557,774, in which fold-back flaps engaging the lateral edges of the pad are constituted by the material of the outer sheet of the nappy-pants, consists in the fact that the fold-back flaps are constituted by a sheet whose only function is leakproofing and which can therefore have a thickness which is markedly lower than an outer sheet which is also to serve as support (for example approximately 10 $\mu$m instead of approximately 20 to 30 $\mu$m for an outer sheet), resulting in a reduction in the cost of the nappy-pants.

I claim:

1. A diaper comprising
   liquid-impervious supple outer sheet whose inner face is provided with lengthwise lines of adhesive,
   an absorbent pad arranged on the inner face of said outer sheet so that its two opposed lengthwise edges are set back relative to the two opposed lengthwise edges of the outer sheet and so that its two opposed transverse edges are set back relative to the two opposed transverse edges of the outer sheet,
   a liquid-pervious supple inner sheet covering the inner face of the outer sheet and the absorbent pad arranged on said face,
   at least one lengthwise-extending elastic member secured by adhesive bonding in the stretched state onto the inner face of the outer sheet, along the median part of each of the two opposed lengthwise edges of said sheet, and
   fastening means for closing the diaper around the user's body,
   wherein a strip of liquid-impervious supple sheet material is placed on the inner face of the outer sheet, below the absorbent pad, over each of the at least one elastic member, over the entire length of the outer sheet, each strip being secured to the outer sheet by at least one of said lengthwise lines of adhesive on both sides of each corresponding elastic member, thus forming with the outersheet, around the corresponding elastic member, a tunnel extending about the entire length of the diaper, and having over its entire length a portion extending laterally beyond the corresponding lengthwise edge of the pad, the said portion being folded onto the top face of the pad so as to envelop said lengthwise edge of the pad, the outer face of inner sheet being coated with adhesive over the entire periphery so as to adhere, all around the pad, onto the outer sheet and onto the strips where the said strips extend beyond the absorbent pad.

2. A diaper as in claim 1 wherein said absorbent pad includes material in particulate form, especially superabsorbent material in granular form.

3. A method for continuous manufacture of diapers comprising:
   unwinding and longitudinally feeding a continuous band of liquid-impervious sheet,
   continuously applying transversely spaced lengthwise lines of adhesive onto the upper face of the said impervious band,
   unwinding and longitudinally feeding continuous elastic members, coating the said elastic members with adhesive at intervals to form adhesive-coated sections separated by sections which are not coated with adhesive and applying the elastic members in the stretched state onto the upper face of the impervious band, in the vicinity of the two opposed lengthwise edges of the latter, between said lengthwise lines of adhesive, so as to make the elastic members adhere thereto along successive longitudinally spaced sections, continuously unwinding and longitudinally applying onto the upper face of the impervious band, over each of the elastic members, a continuous strip of sheet material, each strip having a width greater than the width of the corresponding elastic member, so that each strip adheres to the impervious band along at least one of said lengthwise lines of adhesive on both sides of the corresponding elastic member, and having over the entire length of each strip a portion extending laterally beyond the corresponding edge of said band, successively depositing onto the upper face of the impervious band, over the two strips, individual absorbent pads of a width smaller than the width of the band, so that the successive pads are arranged on the impervious band in the regions where the elastic members adhere to the band, and are longitudinally spaced from each other, folding the extending portion of each strip over the corresponding edge and onto the top face of each pad so as to envelop the edge of the pad, unwinding and longitudinally feeding a continuous liquid-pervious band having substantially the same width as the impervious band, coating the said pervious band with adhesive on one face and applying it with said adhesive-coated face onto the upper face of the impervious band, over the strips and the absorbent pads so that the pervious band adheres all around the absorbent pads, to the impervious band and to the strips where the said strips extend beyond and over the edge of the absorbent pads, and successively cutting off, in the transverse direction, the two bands, the stretched elastic members, and the two strips, between the successive pads, across the sections of the elastic members which are not coated with adhesive.

4. Method according to claim 3, wherein the pervious band is coated with adhesive according to a repetitive pattern in the shape of a closed frame surrounding a window, each window which is not coated with adhesive coming into place over an absorbent pad and the adhesive-coated frame adhering to the impervious band and to the strips around the absorbent pad.

* * * * *

BEST AVAILABLE COPY

UNITED STATES PATENT AND TRADEMARK OFFICE
CERTIFICATE OF CORRECTION

PATENT NO. : 4,917,695
DATED : April 17, 1990
INVENTOR(S) : Villez, Yves

It is certified that error appears in the above-identified patent and that said Letters Patent is hereby corrected as shown below:

Column 7, line 28 (page 12, line 1 of specification) "from" should read --form--.

Signed and Sealed this

Twenty-sixth Day of May, 1992

Attest:

DOUGLAS B. COMER

Attesting Officer  Acting Commissioner of Patents and Trademarks